United States Patent [19]
Williams et al.

[11] Patent Number: 5,964,730
[45] Date of Patent: *Oct. 12, 1999

[54] PROTECTIVE SHEATH FOR CATHETER BALLOONS

[75] Inventors: Kerry Williams, Murieta; Rebecca Ien Tavish, Milpitas; Lawrence E. Howard, Escondido; Udayan G. Patel, San Jose, all of Calif.

[73] Assignee: Advanced Cardiovascular Systems, Inc., Santa Clara, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/920,988

[22] Filed: Aug. 29, 1997

Related U.S. Application Data

[62] Division of application No. 08/698,149, Aug. 15, 1996, Pat. No. 5,808,707.

[51] Int. Cl.[6] .................................................. A61M 29/00
[52] U.S. Cl. ............................................ 604/103; 606/108
[58] Field of Search .................... 604/96, 103; 606/194, 606/192, 108

[56] References Cited

U.S. PATENT DOCUMENTS

| | | | |
|---|---|---|---|
| 4,540,404 | 9/1985 | Wolvek | 604/96 |
| 4,710,181 | 12/1987 | Fuqua | 604/280 |
| 4,738,666 | 4/1988 | Fuqua | 604/280 |
| 5,053,007 | 10/1991 | Euteneuer | 604/96 |
| 5,066,298 | 11/1991 | Hess | 606/194 |
| 5,116,318 | 5/1992 | Hillstead | 604/96 |
| 5,147,302 | 9/1992 | Euteneuer et al. | 604/103 |
| 5,352,236 | 10/1994 | Jung et al. | 606/194 |
| 5,395,334 | 3/1995 | Keith et al. | 606/194 |
| 5,409,495 | 4/1995 | Osborn | 606/108 |
| 5,417,707 | 5/1995 | Parkola | 606/194 |
| 5,425,710 | 6/1995 | Khair et al. | 604/96 |
| 5,569,184 | 10/1996 | Crocker et al. | 604/96 |
| 5,593,412 | 1/1997 | Martinerz et al. | 606/108 |

FOREIGN PATENT DOCUMENTS

| | | |
|---|---|---|
| 0 553 960 A1 | 1/1993 | European Pat. Off. . |
| 2 025 233 | 4/1979 | United Kingdom . |
| WO 96/40349 | 12/1996 | WIPO . |

*Primary Examiner*—Michael Buiz
*Assistant Examiner*—Kevin Truong
*Attorney, Agent, or Firm*—Heller Ehrman White & McAuliffe

[57] ABSTRACT

A polymeric heat shrinkable tubular sheath for mounting about a balloon on a dilatation catheter by heat treating at a temperature which does not detrimentally effect the properties of the balloon to shrink the sheath onto the balloon. The tubular sheath is preferably heated to a temperature above body temperature, e.g. 40<100° C., preferably less than 85° C., to heat shrink the sheath onto the balloon. A presently preferred polymeric material is a copolymer of ethylene (75%) and methyl acrylate (25%). The heat shrinkable sheath has an inner lumen with minimum dimensions large enough to facilitate the advancement of the sheath over the exterior of a dilatation balloon without the need for a great deal of manual manipulation by the physician or other operator prior to heat shrinking.

12 Claims, 2 Drawing Sheets

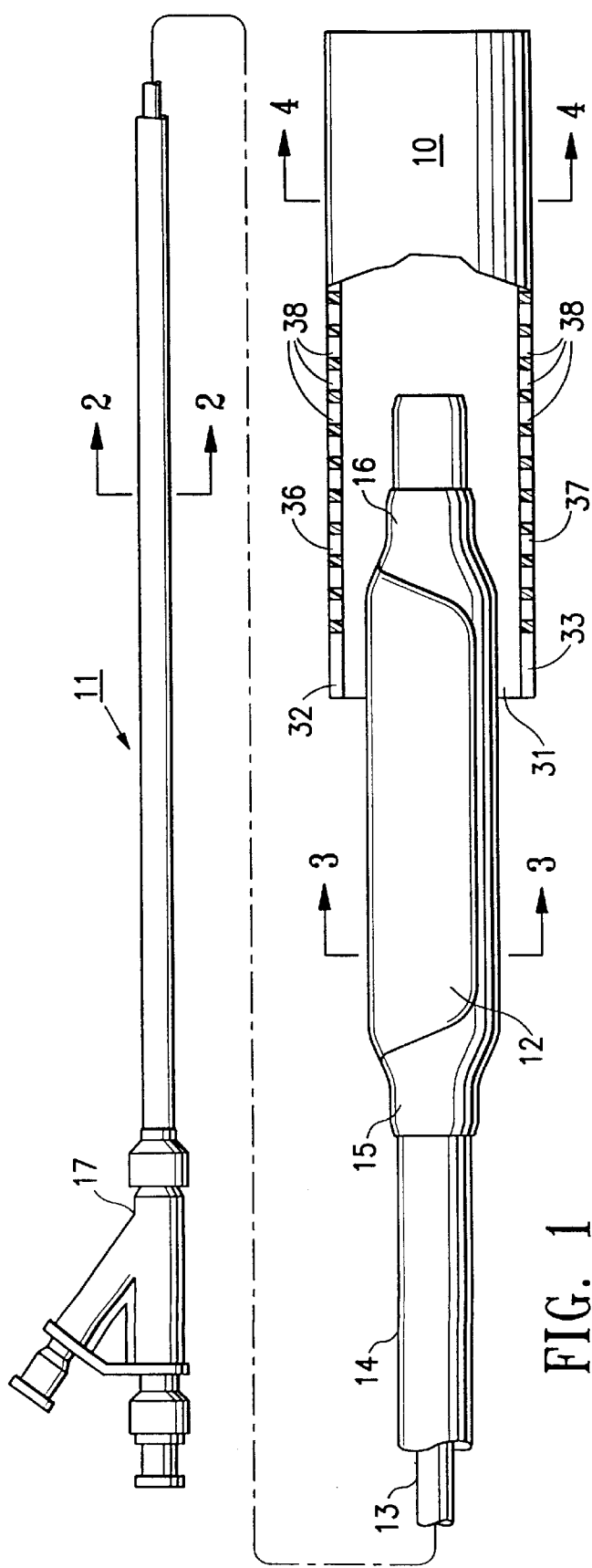
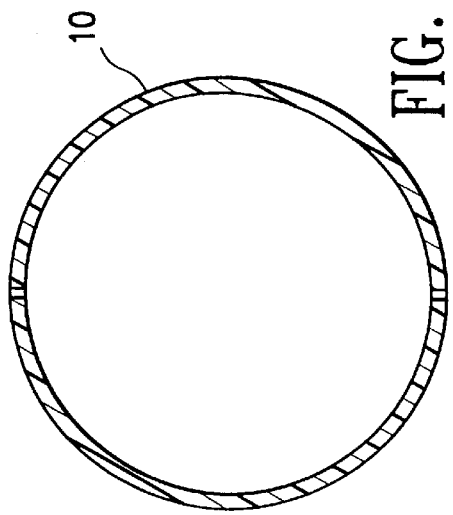
FIG. 4
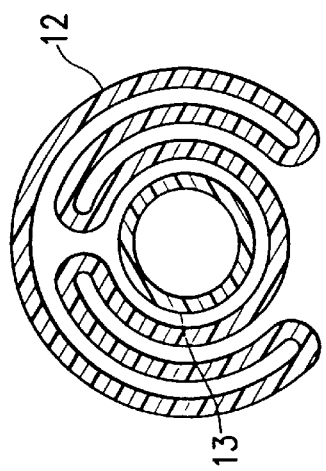
FIG. 3
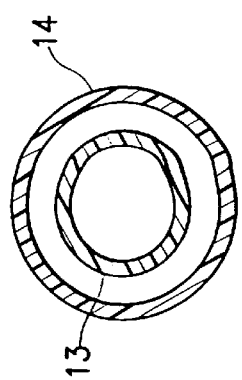
FIG. 2
FIG. 1

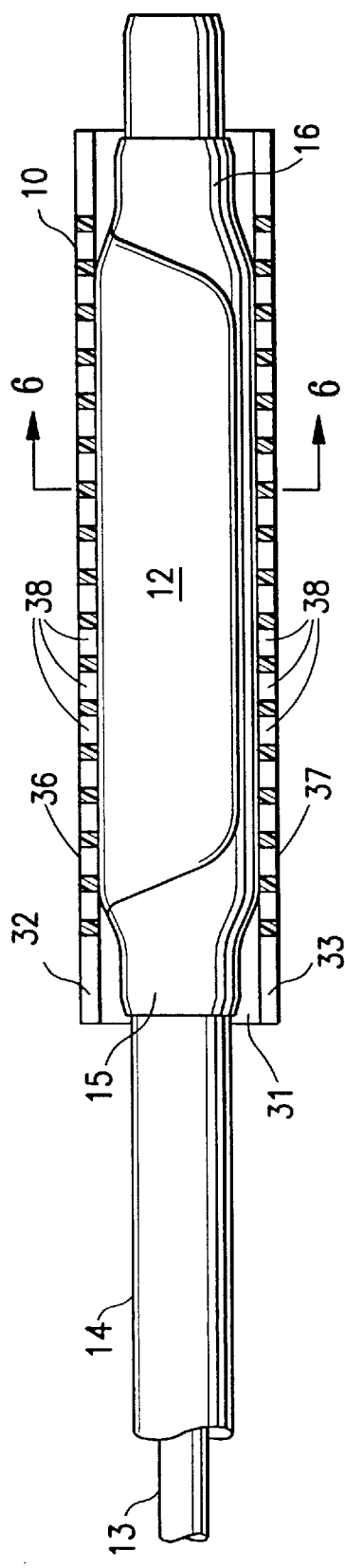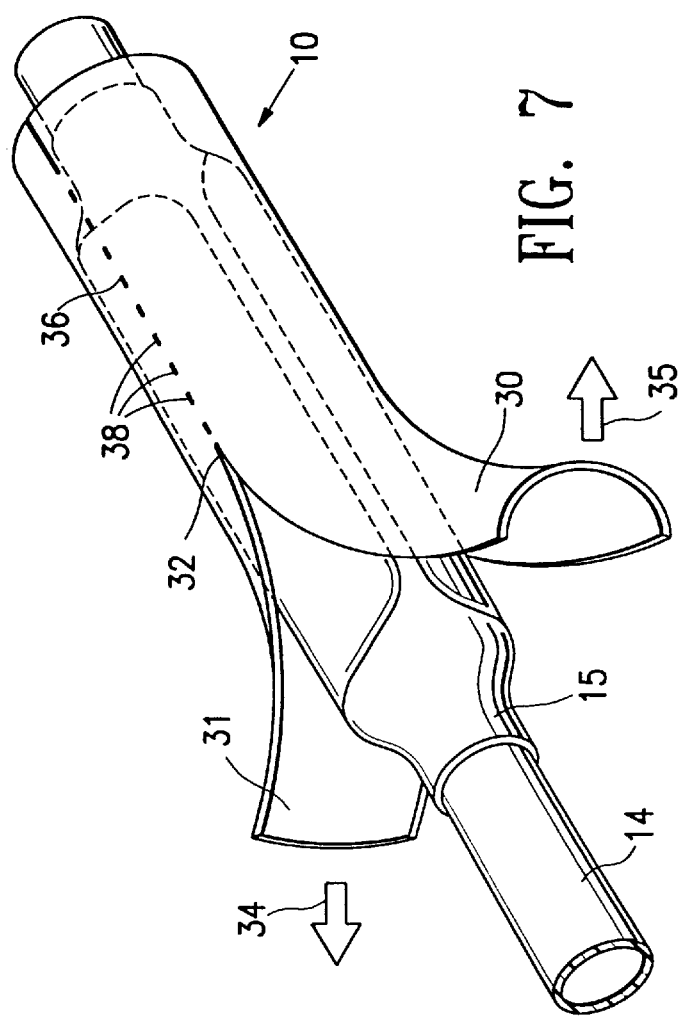

PROTECTIVE SHEATH FOR CATHETER BALLOONS

This is a divisional application of application 08/698,149 which was filed on Aug. 15, 1996 now U.S. Pat. No. 5,808,707.

BACKGROUND OF THE INVENTION

This invention generally relates to the field of intravascular catheters and particularly balloon catheter suitable for coronary angioplasty procedures, PTCA, which is now one of the most widely used treatment modalities for heart disease, basically comprises advancing a dilatation catheter, having an inflatable balloon on its distal extremity, into the patient's coronary anatomy, usually over a guidewire, until the balloon of the dilatation catheter is properly positioned across the lesion to be dilated. Once properly positioned, the dilatation balloon is inflated one or more times with liquid to a predetermined size at relatively high pressures, e.g. up to 20 atmospheres or more, to expand the arterial passageway. Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

In essentially all PTCA procedures, a guiding catheter having a preshaped distal tip is first percutaneously introduced into the cardiovascular system of a patient by a conventional Seldinger technique and advanced therein until the preshaped distal tip of the guiding catheter is disposed within the ascending aorta adjacent to the ostium of the desired coronary artery. The guiding catheter is twisted or torqued from its proximal end, which extends out of the patient, to guide the distal tip of the guiding catheter into the desired coronary ostium. Once the guiding catheter is in proper position within the patient's vasculature, the dilatation catheter is positioned within the inner lumen of the guiding catheter with a guidewire slidably disposed within an inner lumen of the dilatation catheter. The guidewire is first advanced out the distal tip of the guiding catheter seated in the coronary ostium into the patient's coronary artery and directed to the region of the patient's coronary anatomy where the procedure is to occur. A torque is applied to the proximal end of the guidewire, which extends out of the proximal end of the guiding catheter, to guide the curved or otherwise shaped distal end of the guidewire into a desired branch of the coronary artery. The advancement of the guidewire within the selected artery continues until it crosses the lesion to be dilated. The dilatation catheter is then advanced over the previously advanced guidewire, until the balloon on the distal extremity of the dilatation catheter is properly positioned across the lesion which is to be dilated.

With rapid exchange type catheters, which have relatively short guidewire receiving inner lumens in their distal extremities, The guidewire is first advanced through the guiding catheter and out into the coronary anatomy until the distal end of the guidewire is disposed beyond the stenotic site in the patient's coronary artery. The rapid exchange type catheter is then advanced over the guidewire until the balloon is properly disposed within the stenotic site where the dilatation is to occur.

It is conventional practice to fold the deflated balloon about the tubular inner member of the catheter and then advance a protective sheath with an inner diameter larger than the outer diameter of the folded balloon over the folded balloon to hold the balloon in the folded condition for subsequent packaging and sterilization. In addition to protecting the balloon in storage and transit, the sheath holds the folded balloon in position so that, when sterilized at elevated temperatures, the balloon is heat set in the folded condition. A folded balloon presents a much smaller profile than an unfolded balloon and thus is more easily advanced thorough a patient's vascular system. Moreover, being heat set in the folded condition, the balloon returns to the folded condition when subjected to a vacuum after being inflated, such as when venting air from the interior of the balloon and catheter. To facilitate advancing the protective sheath over a folded balloon the sheath is frequently formed of a lubricous fluoropolymer material. Unfortunately, the fluoropolymer protective sheath is usually quite hard and it does not conform to the shape of the folded balloon, so care must be exercised in advancing the sheath over the folded balloon on the catheter and in subsequent handling so that the balloon is not damaged by the protective sheath.

Protective sheaths are described in numerous U.S. Patents, for example, U.S. Pat. No. 5,425,710 (Khair et al.), U.S. Pat. No. 5,033,007 (Euteneuer), U.S. Pat. No. 4,710,181 (Fuqua), U.S. Pat. No. 4,738,666 (Fuqua), U.S. Pat. No. 4,540,404 (Wolvek), U.S. Pat. No. 5,066,298 (Hess), U.S. Pat. No. 5,116,318 (Hillstead) and U.S. Pat. No. 5,417,707 (Parkola). All of the above references are incorporated herein by reference.

While there have been much development effort in protective sheaths for balloons and catheters, none of the sheaths heretofore developed have been completely satisfactory. These prior sheaths have been either very difficult to slide over or otherwise apply to a folded balloon, or they have been difficult to remove from the balloon before the catheter is inserted into the patient. The present invention provides a protective sheath which eliminates or minimizes the problems of these prior sheaths.

SUMMARY OF THE INVENTION

This invention is directed to an improved protective sheath for a balloon catheter which is in a heat shrinkable condition and which has an inner lumen with transverse dimensions sufficiently larger than the outer transverse dimensions of a balloon over which the sheath is to be deployed to allow the sheath to be readily advanced over the balloon. The minimum inner dimension of the heat shrinkable protective sheath should be larger than the maximum transverse dimension and is preferably at least 125% but not more than about 200% of the largest outer transverse dimension of the balloon over which it is to be disposed. The sheath should be heat shrinkable at a temperature above body temperature. However, the heat shrink temperature is generally not greater than 100° C., preferably it is about 40° to about 85° C., to avoid detrimentally affecting the properties and characteristics of polymer materials from which most presently available balloons are made. For ready advancement over the folded balloons of most commercially available dilatation catheters, heat shrinkable sheaths with inner diameters of about 0.025 to about 0.1 inch (0.6–2.5 mm), preferably about 0.04 to about 0.08 inch (1–2 mm) have been found suitable.

The protective balloon sheath of the invention is preferably formed by extruding a suitable polymer material into a tubular form, cross-linking the extruded tubular form by radiation, e.g. E-beam, or by other suitable means and then expanding the cross-linked tubular form to an expanded protective sheath with a requisite inner diameter. For effective heat shrinking the extruded tube should have an inner lumen with a minimum dimension less than the maximum dimension of the balloon over which the sheath is to fit to ensure that, when the sheath is heat shrunk, the inner dimensions of the inner lumen of the heat shrunk sheath will be smaller than the outer dimensions of the balloon to provide a tight fitting sheath. For suitable compression of the balloon, the inner transverse dimensions of the extruded tubular member from which the heat shrinkable protective sheath is formed should be not more than about 90%, preferably not more than about 75% of the maximum outer dimension of the balloon. The expanded heat shrinkable sheath should be heat shrinkable to transverse dimensions which are at most 40%, preferably less than 30% of the folded balloon profile Usually, the balloon is folded about an inner tubular member of the catheter which extends through the interior of the balloon to reduce the profile of the balloon and thereby facilitate entry into the patient. The folded balloon can take a variety of transverse shapes including circular, oval, ovoid and the like. The sheath may be similarly shaped. However, notwithstanding the transverse cross-section shape of the balloon, the expanded but unshrunk protective sheath should have an interior cavity of a size and shape which will readily accept the balloon whatever the balloon's shape.

To facilitate removing the sheath to inflate the balloon prior to venting entrapped air within the catheter, one presently preferred embodiment of the balloon sheath of the invention is provided with at least one, preferably two, longitudinally oriented tear lines or strips so that upon tearing the heat shrunk sheath along the tear lines or strips, it can be readily removed from the balloon without unfolding or damaging the balloon. Additionally, opposing slits may be formed in one end of the sheath to provide a pair of tabs which can be used to tear the sheath or peel the sheath off of the balloon. A series of perforations may be provided in the wall of the sheath along a length thereof to form a tear line. A variety of other means for removing the heat shrunk sheath from the balloon may be employed.

The heat shrinkable sheath should be made from polymer materials which allow the sheath to be heat shrunk onto the balloon at a temperature which will not detrimentally effect the properties of the balloon. Temperatures above 85° C. and particularly above 100° C. will reduce the mechanical properties of most conventional polymeric materials used in dilatation balloons. The polymer material for the sheath should have a Vicat softening point sufficiently below the softening point of the balloon material so that the expanded sheath will shrink to dimensions smaller than the balloon over which the sheath is mounted. Typically, the polymer material of the sheath should have a Vicat softening point less than 50° and a melt index less than 25. The tensile strength of the material should be sufficient to compress the balloon upon heat shrinking of the sheath about the balloon. A wide range of polymeric material may be employed to form the sheath of the invention. Suitable polymers include low density polyethylene (LDPE), linear low density polyethylene (LLDPE), ethylene vinyl acrylate (EVA), ethylene methacrylate (EMA), ethylene methacrylic acid (EMAA) and ethyl glycol methacrylic acid (EGMA). A particularly suitable polymer material for the protective sheath of the invention is a copolymer of ethylene and methyl acrylate which is available under the trademark Lotryl 24MA005 from Elf Atochem. This copolymer contains about 25% methyl acrylate, has a melt index of about 0.5 and a Vicat softening temperature of about 43° C.

The protective balloon sheath of the invention is more easily formed and applied to folded balloons than prior sheaths and, additionally, it allows the balloon to be heat set in a tightly folded condition when sterilized, thereby enhancing the refolding of the balloon after inflation and the recrossing characteristics of the refolded balloon. These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a dilatation catheter with an expanded sheath being advanced over the folded balloon of the dilatation catheter.

FIG. 2 is a transverse cross-sectional view of the catheter shown in FIG. 1 taken along the lines 2—2.

FIG. 3 is a transverse cross-sectional view of the catheter shown in FIG. 1 taken along the lines 3—3.

FIG. 4 is a transverse cross-sectional view of the sheath shown in FIG. 1 taken along the lines 4—4.

FIG. 5 is an elevational view, partially in section, of the distal section of the catheter shown in FIG. 1 with the sheath heat shrunk onto the folded balloon.

FIG. 6 is a transverse cross-sectional view of the catheter shown in FIG. 5 taken along the lines 6—6.

FIG. 7 is a perspective view of a protective sheath being removed from the folded balloon of a dilatation catheter.

DETAILED DESCRIPTION OF THE INVENTION

Reference is made to FIG. 1 which illustrates the advancement of a sheath 10 over the distal section of dilatation catheter 11 having a folded balloon 12. As shown in more detail in FIGS. 2–4, the catheter 11 has an inner tubular member 13 and an outer tubular member 14 forming the catheter shaft proximal to the balloon 12. The balloon 12 has a proximal end 15 which is secured to the distal end of the outer tubular member 14 and a distal end 16 which is secured to the distal end of inner tubular member 13. An adapter 17 is secured to the proximal ends of the inner and outer tubular members 13 and 14 by suitable means such as an adhesive, fusion welding (e.g. laser welding) or heat shrinking. These same means may also be employed to secure the ends of the balloon 12 to the distal ends of the inner and outer tubular members 13 and 14.

FIGS. 5 and 6 illustrate the sheath 10 heat shrunk onto the folded balloon 12. While not shown in the drawings, the heat shrunk sheath 10 applies pressure to the folded balloon 12 to facilitate heat setting the balloon in the folded shape when the catheter is sterilized, so that when the balloon is inflated for venting and then evacuated, it returns to the folded condition.

Removal of the sheath 10 from the folded balloon 12 is demonstrated in FIG. 7. The tabs 30 and 31 formed by the slits 32 and 33 formed in the proximal end of the sheath 10 are pulled as indicated by arrows 34 and 35 to tear the sheath along the tear lines 36 and 37. A plurality of perforations 38 are provided along the tear lines 36 and 37 to facilitate a clean separation of the two halves of the sheath.

While separate balloon sheaths may be prepared for each size balloon, it has been found that usually not more than two sizes of heat shrinkable sheaths are needed for the entire range of balloons profiles typically found in dilatation catheter, i.e. balloons with inflated diameters from about 0.5 to about 4 mm. A first, smaller sized sheath has an inner diameter of about 0.8 inch (20 mm) and a second, larger sized sheath of the preferred material has an outer diameter of about 0.95 inch (24 mm). The wall thickness of the sheath will depend upon the tensile strength of the heat shrunk material and the needs to compress the balloon sheathed. The length of the sheath should be greater than the maximum balloon length so that at least one end of the sheath can be grasped by an operator for removal. Typical sheath lengths will be about 1 to 25 cm, usually about 2 to 5 cm.

EXAMPLE

An ethylene-methyl acrylate copolymer resin sold under the trademark Lotryl 24MA005 from Elf Atochem was extruded into a tubular form having an inner diameter of 0.012 inch and an outer diameter of about 0.037 inch. The extruded tube was irradiated with a dose of 29 mrads of electron beam (E-beam) radiation. Tubular sections of about 7 cm in length were removed from the specimen and the removed tubular sections were expanded to sheaths with inner diameters of about 0.08 inch and outer diameters of about 0.085 inch by subjecting the extruded tubular section to an internal fluid pressure of about 40 psi at a temperature of about 138° C. One end of each of the expanded sheaths were slit a distance of about two centimeters and then each of the expanded sheaths were mounted over folded balloons of a commercially available dilatation catheter having an inflated diameters of 1.5, 3.0 and 4.0 mm. The maximum outer dimension of the folded balloons were about 0.047, 0.053 and 0.062 inch (1.2, 1.35 and 1.6 mm respectively). The expanded sheaths were then heated to 65° C. to heat shrink the sheaths onto the folded balloons. After cooling and sterilization, the sheaths were split by pulling the tabs formed by the slit in one of the ends of the sheaths to remove them from the balloon.

While the description of the invention has been directed herein to certain preferred embodiments, those skilled in the art will recognize that various changes and modifications can be made without departing from the scope of the invention.

What is claimed is:

1. A heat shrinkable polymeric balloon sheath for a catheter balloon, comprising an inner lumen with a minimum inner diameter before heat shrinkage which is at least 125% larger than a maximum outer diameter of the uninflated catheter balloon and after heat shrinkage which is smaller than the maximum outer diameter of the uninflated catheter balloon so that the sheath after heat shrinkage is configured to be tightly fitting around a circumference of the uninflated catheter balloon, and having a proximal section, a distal section, and a continuous cylindrical section extending from the proximal section to the distal section of the sheath, and a weakened sheath wall portion along at least a length thereof to provide tear away characteristics.

2. The balloon sheath of claim 1 wherein the sheath has a length of at least 10 mm.

3. The balloon sheath of claim 1 wherein the sheath has a length of up to 100 mm.

4. The balloon sheath of claim 1 wherein the minimum dimensions of the inner lumen are about 0.04 to about 0.08 inch.

5. The balloon sheath of claim 1 wherein the sheath is formed of a copolymer of ethylene and methyl acrylate.

6. The balloon sheath of claim 5 wherein the copolymer contains about 15 to about 35% methyl acrylate.

7. The balloon sheath of claim 1 wherein the sheath is formed by extruding a suitable polymeric material into a tubular form having an interior, cross-linking the polymeric material and expanding the tubular form by introducing high pressure fluid into the interior of the tubular form at elevated temperature.

8. The balloon sheath of claim 7 wherein the fluid introduced into the interior of the tubular form is at a pressure of about 15 to about 35 psi.

9. The balloon sheath of claim 7 wherein the polymeric material thereof is cross-linked by irradiation.

10. The balloon sheath of claim 1 wherein the minimum inner diameter of the balloon sheath before heat shrinkage is not more than about 200% larger than the maximum outer diameter of the uninflated catheter balloon.

11. A sheath for a catheter balloon having an elongated cylindrical working section, comprising:

a heat shrinkable polymeric balloon sheath disposed about the elongated cylindrical working section of the balloon, having an inner lumen with a minimum inner diameter before heat shrinkage which is at least 125% larger than a maximum outer diameter of the uninflated catheter balloon and after heat shrinkage which is smaller than the maximum outer diameter of the uninflated catheter balloon so that the sheath after heat shrinkage is configured to be tightly fitting around a circumference of the uninflated catheter balloon, and having a proximal section, a distal section, and a continuous cylindrical section extending from the proximal section to the distal section of the sheath, and a weakened sheath wall portion along at least a length thereof to provide tear away characteristics.

12. A sheathed catheter balloon, comprising
a) a catheter balloon having an elongated cylindrical working section; and
b) a heat shrinkable polymeric balloon sheath disposed about the elongated cylindrical working section of the balloon, having an inner lumen with a minimum inner diameter before heat shrinkage which is at least 125% larger than a maximum outer diameter of the uninflated catheter balloon and after heat shrinkage which is smaller than the maximum outer diameter of the uninflated catheter balloon so that the sheath after heat shrinkage is configured to be tightly fitting around a circumference of the uninflated catheter balloon, and having a proximal section, a distal section, and a continuous cylindrical section extending from the proximal section to the distal section of the sheath, and a weakened sheath wall portion along at least a length thereof to provide tear away characteristics.

* * * * *